US00PP12652P2

(12) United States Plant Patent
Saville

(10) Patent No.: US PP12,652 P2
(45) Date of Patent: May 28, 2002

(54) MINIATURE ROSE PLANT NAMED 'SAVACON'

(76) Inventor: John M Saville, 13 Roosevelt Pl., Newburyport, MA (US) 01950

( * ) Notice: Subject to any disclaimer, the term of this patent is extended or adjusted under 35 U.S.C. 154(b) by 0 days.

(21) Appl. No.: 09/550,021

(22) Filed: Apr. 14, 2000

(51) Int. Cl.[7] ..... A01H 5/00

(52) U.S. Cl. ..... Plt./117

(58) Field of Search ..... Plt./117, 116, 118

*Primary Examiner*—Bruce R. Campell
*Assistant Examiner*—June Hwu

(57) ABSTRACT

'SAVacon' is a new and distinct variety of miniature rose plant primarily identified by its near white buds opening flat to near white flowers with intense fragrance and its glossy dark green foliage on a compact plants.

1 Drawing Sheet

CROSS REFERENCE

This present invention relates to a new and distinct variety of hardy, bush type plant of the miniature rose class, whose near white flowers bear some resemblance in form only to those of its seed parent, 'SAVasach' (U.S. Plant Pat. No. 5,967; 'Sachet') but being slightly larger when full open. The distinguishing characeristics between this new miniature rose plant and other varieties of which I am aware with a similar near white coloration are its strong fragrance, the size and form of its bloom on a plant of compact bushy habit.

RIGHTS TO THE INVENTION

Be it known that John M. Saville claims new and useful improvements in ROSE PLANT/Var.SAVacon and following is a clear and exact description of the same.

BACKGROUND OF THE INVENTION

The present invention relates to a new and distinct variety of hardy, dwarf, bush type rose of the miniature rose class, *Rosa chinensis 'Minima',* having a very fragrant flower and being a plant which grows and blooms satisfactorily both in the greenhouse and outdoors; provides decoration as a garden perennial or specimen plant; and is good for growing in containers with protection recommended through the winter in severe climates.

The present variety of miniature rose was created in a greenhouse in Rowley, Mass., under conditions of careful control and observation by crossing the following two rose plants:

The seed parent is 'SAVasach' (U.S. Plant Pat. No. 5,967; 'Sachet'), a miniature rose plant of spinel red coloring and strong fragrance.

The pollen parent is 'MACgenev' (U.S. Plant Pat. No. 8,279; 'Aoteara-New Zealand', 'New Zealand') a hybrid tea rose of mainly apricot coloration and strong fragrance.

The blooms of this new invention are similar to those of its seed parent, 'SAVasach', only in petal form and the way the flowers open but being slightly larger in size. The fragrance of this new invention is similar to but stronger than that of its seed parent, 'SAVasach' and different from but as strong as that of its pollen parent, 'MACgenev'.

Asexual propagation by cuttings of this new variety shows that all distinguishing characteristics of this rose continually come true to form.

SUMMARY OF THE INVENTION

The present invention relates to a new and distinct variety of the miniature rose class being primarily characterized — as to novelty — by fragrance in a miniature rose of this coloring, which is near white.

The variety is further characterized by:

An abundance of recurrent bloom, with flowers most often borne singly.

A plant which is vigorous, upright and somewhat spreading yet compact, with dark green glossy foliage.

Very few thorns.

BRIEF DESCRIPTION OF THE DRAWING

The accompanying color photograph shows specimens of the flower of this new variety in different stages of development as grown inside, under plastic in May in Essex County, Mass.

BOTANICAL DESCRIPTION OF THE PLANT

Following is a detailed description in outline form pertaining specifically to this new and distinct variety of miniature rose plant, as observed on 3 year old plants grown inside under plastic in 1.8 gallon containers. All major color plate identifications made are referring to The Royal Horticulture Society Colour Chart except where common terms of color definition are employed.

*Rosa chinensis* 'Minima', miniature rose.

Seed parent: 'SAVasach' (U.S. Plant Pat. No. 5,967; 'Sachet')

Pollen parent: 'MACgenev' (U.S. Plant Pat. No. 8,279; 'Aoteara-New Zealand', 'New Zealand')

FLOWERS

Blooming habit: Recurrent.
Borne: Most often singly.

Bud:

*Size.*—Small: to ½ inch just before petals start to unfurl.

*Form.*—Ovate.

*Color.*—When sepals first divide — a near white color with a pale yellow tint, near 11D.

*Sepals.*—Color — reverse is near 146B becoming lighter towards center and base of each individual sepal is near 146D; inside of the sepals' tips is a darker green, near 137B. Characteristics — lanceolate and lightly foliated, extending ½ inch beyond the tip of the bud; as they unfurl, reflexing back to or beyond the stem and remaining attached in full reflex as the hips mature.

Peduncle:

*Length.*—Usually 1 inch.

*Aspect.*—Straight to slightly curved.

*Strength.*—Generally erect.

*Color.*—Near 146C.

*Surface texture.*—Glabrous.

Bloom:

*Size.*—When fully expanded — 2 to 2½ inches.

*Form.*—Urn shaped at first, then becoming near flat with outer petal edges rolling loosely under and stamens showing.

*Petalage.*—35 to 40.

*Petaloids.*—3 to 5.

*Fragrance.*—Strong, sweet, typical rose scent.

*Lasting quality as a cut flower.*—7 days or more.

Petals:

*Texture.*—Smooth and moderately thick.

*Appearance.*—Inside — velvety, outside — satiny.

*Form.*—Broad spatulate, occasionally pointed at apex.

*Size.*—Up to 1⅛ inches wide and 1⅜ inches in length. Petaloids — up to ¾ inch in length and ¼ inch wide.

*Arrangement.*—Arranged shingle-like.

*Color.*—A near white color with a soft yellow tint, near 11D, and being a slightly deeper yellow towards the base of the petals and the center of the flower, near 8D and 12C. The coloring becomes uniformly lighter as the bloom ages and finally to white just before the petals drop.

*Petaloids.*—Have the same color, shape and texture as the petals but only being to ¾ inch in length and not more than ¼ inch wide.

*Persistence.*—Petals drop of clean in 5 to 8 days.

*General tonality.*—Very pale empire yellow to near white.

*General tonality from a distance.*—White.

REPRODUCTIVE ORGANS

Stamens, filaments and anthers:

*Arrangement.*—Unevenly in a single row at the outer edge of the receptacle.

*Quantity.*—Some, about 45.

*Filaments.*—length — varying from about ⅛ inches to about ¼ inches. General color — near 6D.

*Anthers.*—Color — pale yellow, near 13D.

Pollen:

*Color.*—Yellow orange, near 20A.

*Quantity.*—Ample.

Pistils, styles and stigmas:

*Quantity.*—Also about 45.

*Styles.*—Short and uneven in length, thin and a pale lemon yellow at their base and becoming wider and a medium cherry red half way up the length.

*Stigmas.*—Color — a pale salmon color near 27B.

Receptacle:

*Shape.*—Round.

*Size.*—Averaging 5/16 inch in diameter.

*Surface texture.*—Lustrous.

*Color.*—Near 145C.

Hips:

*Shape.*—Cone shaped, inverted; many seeds protrude from the top, occasionally with the hip splitting open.

*Size.*—Averaging ½ inch in diameter.

*Color.*—Currant red, near 46A, where the sun hits it and graduating to near 167C on the underside or shaded side.

*Seeds.*—Surface: glabrous. Color: near 162C and being flushed lightly with varying degrees of a color near 167A; where the seeds protrude from the hips they are near a color between 137A and 147A. Size: medium, being usually between 7/32 and 8/32 inch long, between 3/16 and ¼ inch in width and between ⅛ and ¼ inch in depth.

PLANT

Habit: Upright and somewhat spreading, becoming full when mature. Growth: Vigorous.

*Height.*—20 to 24 inches.

*Width.*—Up to 30 inches.

*Length of flowering stem.*—Varying to 7 inches, most often near 3 inches.

Foliage:

*Size of mature leaf.*—Averaging 3½ inches from attachment at plant stem to tip, measured along the rachis.

*Quantity.*—Abundant.

*Color.*—New foliage — dark green, near 137A and near 183B along the margins and sometimes lightly flushing the entire leaf; underside is a yellowed dark green, near 146C and flushed lightly with near 183B. Old foliage — Upper surface is near 139A and underside is near 147B.

*Texture.*—Upper side is glossy, under side is matte.

*Leaflets.*—Usually 5 leaflets, occasionally 3 to 7. Shape — ovate with acute tip. Size mature terminal leaflet — averaging 1⅜ inches, base to tip. Edge — serrated. Serration — fine and very nearly even.

*Rachis.*—Texture — upper surface is smooth, under surface is smooth but occasionally has a few fine hairs. Colors on old foliage — slightly lighter than the new foliage, near 137B; underside is a lighter yellow green, near 144B.

*Stipules.*—Finely bearded and short, ¼ to ⅜ inch.

Resistance: Very good resistance to mildew; good resistance to blackspot; no rust observed; good resistance to gall; appears to have good resistance to aphids, thrip and spidermite.

Wood: Smooth and medium olive green on both old and new wood, near 146B; new wood may be flushed lightly with near 183B.

Thorns: The first thorns appear on the plant after it is 2 years old and then there may be a few only on the main stalks and laterals.

*Form.*—A flat base tapering to a fine point, being either curved or angled slightly downward.

*Length.*—Short, to no more than 3/16 inch but most often less.

*Color when young.*—A chocolate brown, near 177B and the tip becoming near 146D, and only observed at this coloring.

Winter hardiness: This variety has been tested hardy to zone 4 with ample winter protection.

I claim:

1. A new and distinct variety of hardy miniature rose plant substantially as illustrated and described, characterized by near white buds and flowers of a form similar to those of it's seed parent, 'SAVasach', differing in color, 'SAVasach' being a spinel red, and with a stronger rose fragrance; and further characterized by a plant of upright and spreading habit, with very few and small thorns and dark green glossy foliage; easy to propagate from cuttings; and flowers that are borne mostly singly, and last well as cut flowers.

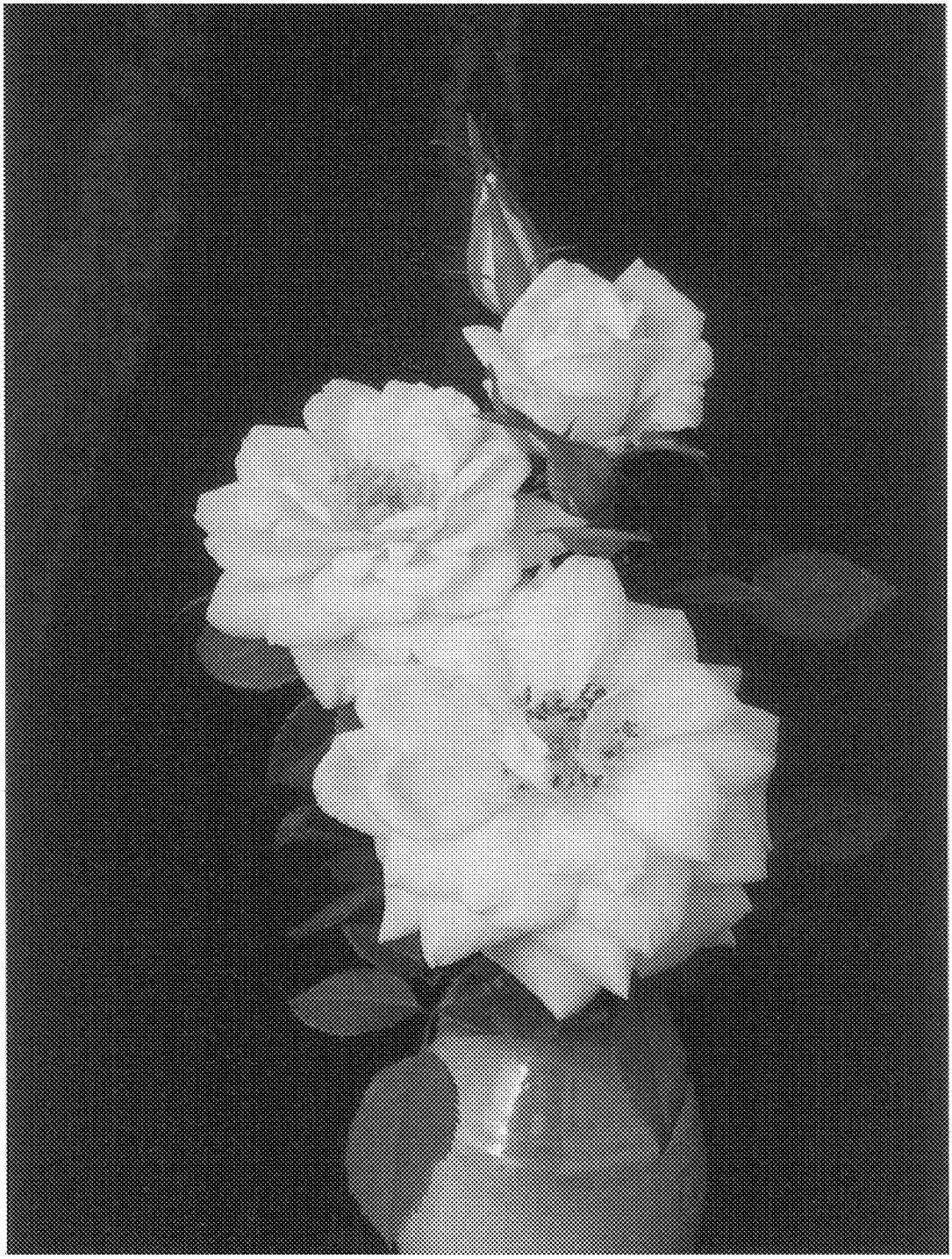

* * * * *